United States Patent [19]

Manning et al.

[11] Patent Number: 5,517,866

[45] Date of Patent: May 21, 1996

[54] ENHANCED RATE MONITOR FOR FLUID SAMPLING

[75] Inventors: Charles R. Manning, Palo Alto; Joyce Chang, Los Altos, both of Calif.

[73] Assignee: Assay Technology, Inc., Palo Alto, Calif.

[21] Appl. No.: 248,072

[22] Filed: May 23, 1994

[51] Int. Cl.$^6$ ............................................. G01N 1/24
[52] U.S. Cl. ................................................. 73/863.21
[58] Field of Search ...................... 73/863.21, 863.23, 73/864.31–864.34; 422/86–88; 55/270, 300, 400, 467, 383

[56] References Cited

U.S. PATENT DOCUMENTS

| | | |
|---|---|---|
| 3,985,017 | 10/1976 | Goldsmith . |
| 4,208,371 | 6/1980 | Kring . |
| 4,235,097 | 11/1980 | Kring et al. . |
| 4,265,635 | 5/1981 | Kring . |
| 4,269,804 | 5/1981 | Kring . |
| 4,328,181 | 5/1982 | Anders et al. . |
| 4,348,358 | 9/1982 | McKee et al. . |
| 4,350,037 | 9/1982 | Higham ............................. 73/863.21 |
| 4,527,953 | 7/1985 | Baker et al. ....................... 73/864.34 |
| 4,528,160 | 7/1985 | Eckstein et al. . |
| 4,783,316 | 11/1988 | Pannwitz . |
| 4,790,857 | 12/1988 | Miksch . |
| 4,801,800 | 1/1989 | Scheible ............................ 73/863.21 |
| 4,961,916 | 10/1990 | Lesage et al. ..................... 73/863.21 |
| 5,000,052 | 3/1991 | Sipin . |
| 5,001,463 | 3/1991 | Hamburger ....................... 73/863.21 |

OTHER PUBLICATIONS

Guild et al., "Bi–Level Passive Monitor Validation: A Reliable Way of Assuring Sampling Accuracy for a Larger Number of Related Chemical Hazards," *Appl. Occup. Environ. Hyg.*, 7(5), pp. 310–317, May 1992.

Harper et al., "An Evaluation of Sorbents for Sampling Ketones in Workplace Air," *Appl. Occup. Environ. Hyg.*, 8(4), pp. 293–304, Apr. 1993.

*Primary Examiner*—Robert Raevis
*Attorney, Agent, or Firm*—Majestic, Parsons, Siebert & Hsue

[57] ABSTRACT

Devices are provided with enhanced rates of sampling in applications such as monitoring of environmental chemical exposure levels. Preferred embodiments include a small motor and power supply, such as a battery, to move an intake surface with respect to the environment, which embodiments may be used as personal monitors. Chemical species collected through the intake surface diffuse to a collector and the collector may be analyzed for concentration of chemical species.

17 Claims, 1 Drawing Sheet

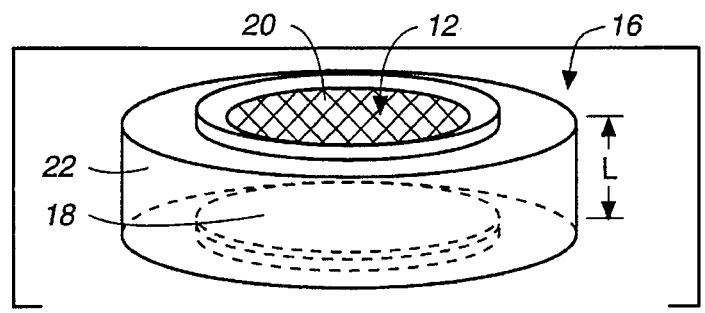
FIG._1
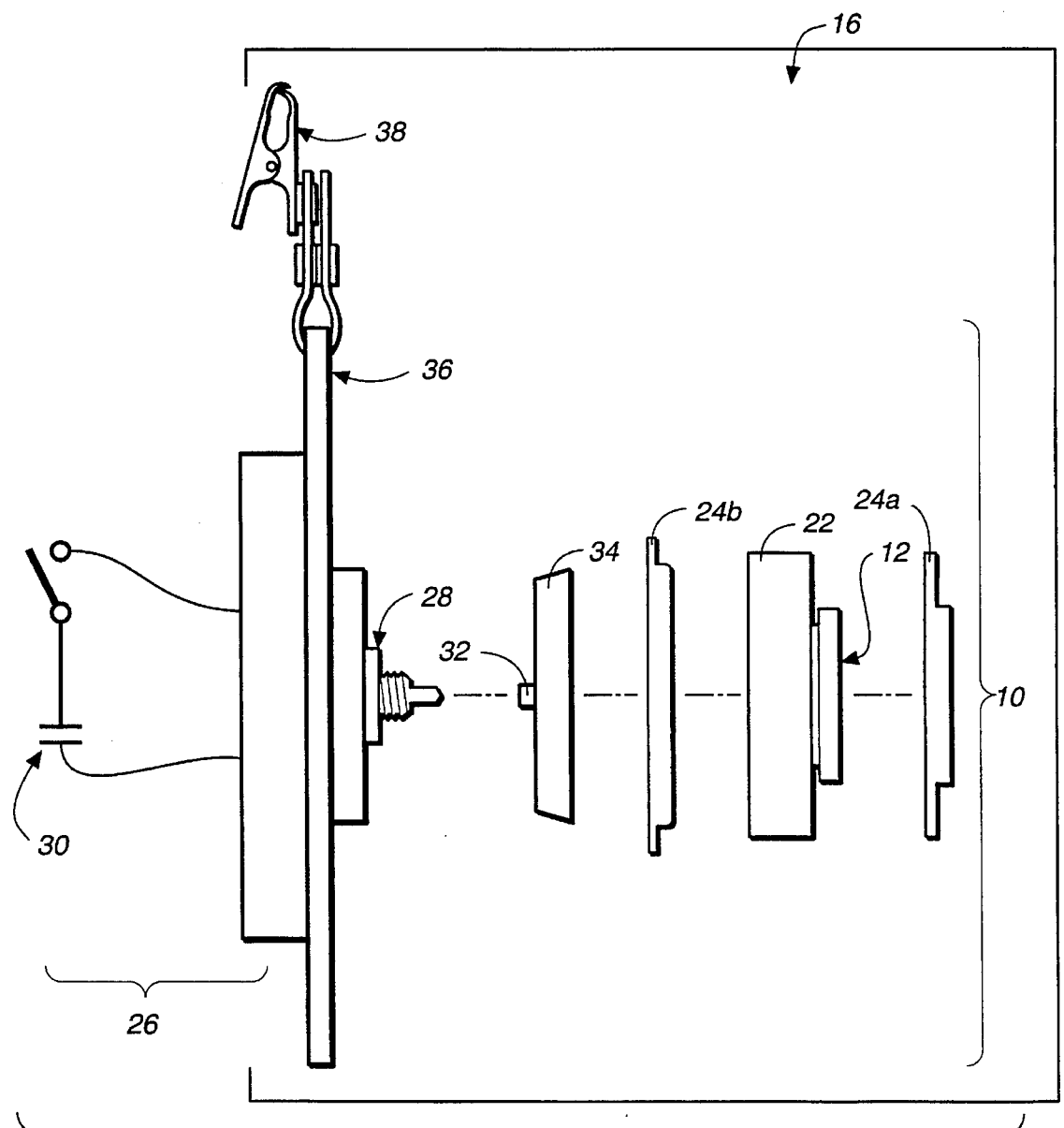
FIG._2

ENHANCED RATE MONITOR FOR FLUID SAMPLING

FIELD OF THE INVENTION

This invention generally relates to monitoring of environmental chemical exposure levels, and more particularly to enhanced rates of sampling and an ability to detect lower contaminant levels by devices that are preferably sufficiently small and portable so as to be personal monitors.

BACKGROUND OF THE INVENTION

The need to monitor and control chemical exposure has increased with concerns about the hazards imposed by chemicals in the environment. Exposure to airborne chemicals is especially hazardous since inhalation is the most efficient mechanism for absorption of chemicals by the body. Accordingly, limits have been placed by regulatory authorities on permissible concentrations of toxic chemicals that may be present in the environment.

In the workplace, where a variety of chemicals are commonly used, more than 600 Permissible Exposure Limits ("PEL") have been established by the U.S. Occupational Safety and Health Administration ("OSHA") under the Occupational Safety and Health Act of 1970. Additional limits to chemical exposure in the general environment have also been set by the U.S. Environmental Protection Agency in the Clean Air Act of 1968.

Since concentrations of chemicals in the workplace may vary from time-to-time and from place-to-place, air monitoring is required by the OSHA to determine whether a workplace is in compliance with Permissible Exposure Limits. Since the primary hazard in such circumstances is inhalation by workers, U.S. regulations specify that air samples taken to demonstrate compliance with Permissible Exposure Limits must measure Time-Weighted Air Concentrations in the worker's "breathing zone," i.e. near to the nose and mouth.

In order to comply with this requirement, air monitoring devices should be light and compact enough to be worn by the worker during work tasks without hampering the worker or inducing any changes which may affect the air sampling process. Ideally, such a "personal monitor," as they are called, should be light and compact enough that the person being monitored quickly loses awareness that a sampling device is being worn.

Environmental air sampling can use pumps to draw air samples though collection devices for analysis. For example, U.S. Pat. No. 5,000,052, issued Mar. 19, 1991, inventor Sitin, describes a sampler device, such as for area monitoring during asbestos removal. However, this sampler device uses area sampler pumps, which are usually relatively large and stationary and are designed to sample much larger volumes of air at high flow rates than personal sampler pumps, which are designed to be worn by an individual being monitored.

Pumps are known and used with monitors worn on the person. Thus, traditional personal air sampling methods developed by the National Institute for Safety and Health ("NIOSH") required belt-mounted air sampling pumps weighing upwards of two pounds, which draw the air sample through a glass tube attached to pocket or lapel. However, such devices have proved to be cumbersome and expensive to use.

Due to their small size (typically, the size of a business card and weighing less than one ounce) and ease of use, diffusive samplers have become more popular than traditional methods using pumps as diffusive samplers permit more convenient personal sampling in compliance with OSHA requirements at a lower cost and with less disruption of the worker performing his/her tasks.

Air monitoring devices which collect a sample via gaseous diffusion have permitted a dramatic reduction in the size of personal samplers. An early personal monitor based on diffusion is described by U.S. Pat. No. 3,985,017, issued Oct. 12, 1976, inventor Goldsmith. Subsequent descriptions of personal air monitoring devices are contained, for example, in U.S. Pat. No. 4,235,097, issued Nov. 25, 1980, inventor Kring et al.; U.S. Pat. No. 4,265,635, issued May 5, 1981, inventor Kring; U.S. Pat. No. 4,348,358, issued Sep. 7, 1982, inventors McKee et al.; and U.S. Pat. No. 4,790,857, issued Dec. 13, 1988, inventor Miksch.

While diffusive samplers, or "passive" samplers as they are often called, have become popular for monitoring chemically exposed workers, sampling pumps have not disappeared due an advantage they retain, namely, that sampling pumps can normally sample at a higher rate (volume of air per unit time) and, consequently, given a comparable sampling time, sampling pumps can normally detect lower levels of air contaminants than diffusive samplers. Presently, as regulators seek to lower chemical exposure levels, the ability to detect and measure lower contaminant levels has become ever more important.

SUMMARY OF THE INVENTION

It is an object of the present invention to provide a fluid sampling device, useful such as for sampling airborne contaminants in proportion to environmental concentrations, where the sampling rate is enhanced while retaining the advantages of small size and economy.

In one aspect of the present invention, a personal monitor comprises a trap having an affinity for airborne contaminants. The trap operates so that air velocity adjacent to the trap is substantially enhanced with respect to the environmental air. Enhancement of air velocity is preferably created with a motor operable at a DC voltage of between about 0.5 and about 10 volts. A motor mount operatively associates the motor with the trap. Such a personal monitor preferably has the motor mount operatively associating the motor with the trap so as to rotate the trap in a carefully controlled manner in order for concentration of the species in the fluid environment that is collected by the trap to be determined or calculated.

In another aspect of the present invention, a particularly preferred environmental fluid sampling device includes a sample collector, or trap, adjacent to an end of a diffusive pathway. The diffusive pathway is defined by a chamber. A fluid permeable surface is carried by the chamber at the beginning of the diffusive pathway and the fluid permeable surface is exposed to the fluid environment. A motor mounted in association with the chamber is operative to move the surface in the fluid environment and/or to move fluid of the environment adjacent to the surface. In this particularly preferred embodiment, the mechanism of gaseous diffusion is used. A motor preferably rotates the surface to create air velocities in excess of about 50 feet per minute at the interface between the permeable surface and the fluid environment, and more typically rotates the surface to achieve air velocities in excess of about 300 feet per minute.

Unlike prior personal monitors using a diffusive mechanism, embodiments of the present invention typically achieve sampling rates per unit area of surface in excess of 10 milliliter per minute per square centimeter of exposed surface, and more typically on the order of 40 or 50 milliliter per minute per square centimeter and greater. Thus, embodiments of the invention may be used to detect airborne contaminants at lower contaminant levels in the same sampling time as prior known devices or to detect contaminant concentrations in less sampling time.

These advantages are particularly important for detecting a contaminant such as a glycol ether, which may be present in concentrations on the order of several hundred parts per billion in processes such as semiconductor manufacturing. Such very low contaminant levels are below the practical sensitivity of presently known personal monitors, yet such contaminants are implicated in or suspected to be a possible factor in increased miscarriage incidents.

Other advantages and objects will become apparent upon reading the following description and the claims.

BRIEF DESCRIPTION OF THE DRAWINGS

FIG. 1 is a perspective view, partially in phantom, of part of an embodiment of the invention; and FIG. 2 is an exploded side view of an inventive embodiment.

DESCRIPTION OF THE PREFERRED EMBODIMENTS

Embodiments of this invention are useful in sampling chemical species or contaminants present in a fluid, typically air and thus are monitors or samplers of environmental fluids. By "fluids" is meant either gas or liquid. A species being sampled in the ambient environment may sometimes be referred to as a gas, or as being in gaseous or vapor form, which are all terms meant to be used interchangeably for purposes of practicing the invention. The invention will be illustrated by reference to air, since preferred embodiments of the invention are personal monitors that are light and compact enough so that the person whose workplace air is being monitored can perform his or her tasks substantially without impediment or even awareness that a sampling device is being worn. For example, particularly preferred embodiments can weigh on the order of only about two ounces (including a motor and battery as will be more fully described hereinafter) and are readily mounted on a worker's clothing by a clip or other fastening device in a manner similar to (or in conjunction with) security identification badges and the like.

Thus, preferred embodiments of the invention are diffusive samplers for sampling fluids, typically air, in which chemicals present in air such as volatile organic compounds or vapors are sampled. Volatile organic compounds such as hydrocarbons ("VOC's") pose contamination problems and can be a health threat. Among volatile organic compound contaminants frequently found in the working environment are those used in paint manufacture (e.g. acetone, methyl isobutyl ketone, toluene, xylene, mineral spirits, naphtha), halogenated hydrocarbons such as trichloroethylene and perchloroethylene, which are common solvent and cleaning agents, and hydrocarbons from petroleum processing or transport. Aspects of this invention will use the following chemical compounds as illustrative: ethyl ether, acetone, methylene chloride, hexane, methyl ethyl ketone, ethyl acetate, tetrahydrofuran, methyl chloroform, heptane, benzene, trichloroethylene, n-propyl acetate, methyl methacrylate, methyl iso-butyl ketone, toluene, butyl acetate, perchloroethylene, xylene, styrene, and cyclohexanone. The "PEL" for each of these is also given hereinafter in Table 3.

Prior known devices have had sampling rates that have been limited under conditions of air velocity in a worker's breathing zone. However, embodiments of this invention have the capacity to be operated with a consistently enhanced velocity of fluid flow provided at an intake surface. In order that a continuous equilibrium can be maintained for any sampling device using diffusion to function properly, one must avoid having the environment adjacent to the intake surface from becoming even temporarily depleted by sampling. If depletion occurs, then the sampler will not accurately measure the bulk concentration of compounds of interest in worker's environment.

Since prior diffusive devices have utilized the normal connection present in typical working environments (due to a worker's movement and air circulatory patterns whether by air conditioning or natural air currents), the sampling rates of known devices have only been on the order of about 5 to 6 cc/min-cm$^2$. Table 1, below illustrates the sampling rates of twenty different volatile species for three commercially available diffusion devices.

TABLE 1

| Species Sampled | Prior Art Devices Sampling Rate (ml/min) per Unit Area (cm$^2$) | | |
| --- | --- | --- | --- |
| | Device 1 | Device 2 | Device 3 |
| Ethyl Ether | 5.26 | 5.54 | 4.25 |
| Acetone | 5.73 | 6.53 | 5.02 |
| Methylene Chloride | 5.41 | 5.91 | 4.55 |
| Hexane | 4.57 | 4.84 | 3.72 |
| Methyl Ethyl Ketone | 5.19 | 5.74 | 4.41 |
| Ethyl Acetate | 4.93 | 5.37 | 4.13 |
| Tetrahydrofuran | 5.31 | 5.59 | 4.29 |
| Methyl Chloroform | 4.41 | 5.16 | 3.97 |
| Heptane | 4.13 | 4.46 | 3.43 |
| Benzene | 5.07 | 6.09 | 4.67 |
| Trichloroethylene | 4.44 | 5.57 | 4.28 |
| n-Propyl Acetate | 4.30 | 4.79 | 3.68 |
| Methyl Methacrylate | 4.54 | 4.79 | 3.68 |
| Methyl iso-Butyl Ketone | 4.29 | 4.53 | 3.48 |
| Toluene | 4.49 | 5.93 | 4.56 |
| Butyl Acetate | 4.51 | 5.21 | 4.01 |
| Perchloroethylene | 4.04 | 4.36 | 3.35 |
| Xylene | 3.90 | 4.68 | 3.60 |
| Styrene | 3.83 | 5.06 | 3.89 |
| Cyclohexanone | 4.13 | 5.30 | 4.07 |

As illustrated by the data of Table 1, all three commercially available personal monitors had sampling rates in the range of about 4 to at best about 6 milliliter per minute per square centimeter.

Particularly preferred embodiments of the invention operate as do the just described, known devices of Table 1 by using the mechanism of gaseous diffusion, which mechanism is described in Fick's laws of diffusion. The diffusion mechanism permits determination of a sampling rate from which concentration of species desired for monitoring in the environment is then calculable when certain dimensions of the sampling device are known.

A normal diffusional sampling rate is determined by the equation ("Formula 1"):

$$\text{Sampling Rate} = (D)(A/L)$$

where D=diffusion co-efficient of component or contaminant through diffuser,

A=cross-sectional area of diffuser openings presented to the sampled fluid, and

L=effective length of diffuser channels or diffusive pathway.

Referring to FIG. 1, a sampling device embodiment 10 has a fluid permeable surface 12 interposed between the environment 16 and a sample collector 18. The distance between surface 12 and sample collector 18 is a minimum distance (L), where (L) is a fluid diffusion pathway as used in the above Formula 1. Fluid introduced from environment 16 at surface 12 diffuses along the pathway to sample collector 18. That is, fluid permeable surface 12 is preferably the interface between environment 16 and a "dead zone" in which diffusion occurs but no convection.

Diffuser

The surface 12 is preferably formed by a member shown as diffuser 20, which may be formed from a variety of materials and have the holes, pores, or interstices that permit diffusion formed by a variety of means. Diffuser 20 preferably has a thickness of between about 0.01 mm to about 3 mm while surface 12 preferably has a surface area of between about 0.1 cm$^2$ to about 10 cm$^2$. Where diffuser 20 is formed of materials having tortuous paths, then "L" in Formula 1 is determined empirically by measuring the sampling rate of the device or by applying other air permeability procedures. Where diffuser 20 is formed of materials having substantially "straight through" holes, then "L" and the average diameter of the particular hole preferably would be in a ratio of about 0.35:1 or less.

For example, diffuser 20 may be prepared by cutting a circular disc 0.02-3 mm in thickness from a variety of commercially-available microporous filters having tortuous paths or having porous, parallel "straight through" holes. Alternately, diffuser 20 may be prepared by separating two microporous filters by a doughnut-shaped, inert, plastic spacer creating a fixed diffusion space between the two filters. Still alternately, diffuser 20 may be prepared by drilling a multiplicity of tubular holes parallel to the direction of diffusion in a disc of inert plastic. A particularly preferred diffuser 20 with a tortuous path is formed by a β-irradiated, chemically etched membrane, such as are commercially available as Nucleopore or Poretics filters.

Alternately, diffuser 20 may be eliminated for certain embodiments so long as surface 12 is moved at controlled rates (so that calculations of species concentrations can be made from the Nerst and Levich equations).

If the effective lengths of channels through the diffuser 20 are shortened, the device 10 samples at successively higher rates; however, the sampling rate achieved would begin to be limited by depletion of fluid in the immediate vicinity of the device because the natural convection at the sampler surface would be unable to supply fresh fluid (i.e., fluid having its normal components and contaminant levels unaffected by sampling) to the sampler surface 12 as rapidly as the sampler collects.

This limitation is a basis for the fact that prior art diffusive air samplers have only utilized sampling rates at or below about 5 or 6 ml per minute per cm$^2$ of exposed sampler surface, as illustrated by the data of Table 1. However, with the higher fluid velocity flows provided by embodiments of the invention across the sampler surface 12, higher diffusive sampling rates can be readily maintained in accordance with devices of this invention.

Chamber

Embodiment 10 preferably includes a chamber 22 in which fluid introduced from the environment at surface 12 diffuses to collector 18. Thus, chamber 22 encloses sample collector 18 and forms a "dead space" in which convection is eliminated and instead diffusion controls the mechanism by which fluid travels to the collector 18. The interior of chamber 22 can be in a wide variety of shapes (e.g. cylindrical, conical, polyhedral).

Chamber 22 can also function to isolate collector 18 from the environment and protect it from contamination before and after the monitoring process. For example, chamber 22 can additionally include, as shown by FIG. 2, a cover or cap 24a that can fasten in place over surface 12 and thus prevent contamination of the collector 18 while cover 24b can releasably fasten onto the bottom of chamber 22 so as to access and remove collector 18 when ready for analysis.

Convection Generator

Continuing with FIG. 2, the dramatically enhanced rates of sampling provided by embodiments of the invention (which also provides an ability to detect lower contaminant levels) are obtained by either moving surface 12 in the fluid environment 16 or moving the environmental fluid 16 adjacent to surface 12 (or both). That is, a convection generator 26 may be viewed either a means to continuously move the surface 12 with respect to the fluid being sampled, or it may be viewed as a means to move the fluid being sampled across the surface 12.

The convection generator 26 may include a motor 28 and a power source such as a battery 30.

Such motors may be used either to rotate the device 10 as depicted in FIG. 1, or to power a fan or stirrer (not illustrated), for all of which a motor 28 generates a fluid velocity across the surface 12 and creates the convection needed to support enhanced rates of diffusion into the device 10. Thus, as shown by FIG. 2, convection generator 26 may be a tiny DC motor 28 attached via motor mount 32 and chuck 34 to the device 10. In one form of the present invention, motor mount 32 and chuck 34 operatably associate the convection generating means 26 so as to rotate the surface 12, via motor 28, to attain the necessary air velocity at the environmental interface. Small motors suitable for use (such as weigh 0.1 to 1 oz.) are commercially available from a number of manufacturers and are capable of generating controlled motor speeds in the range of 100 to 20,000 rpm from a 0.5 to 10 volts DC input. Such motors can operate under a light load (0.1 to 1 in-oz) with power consumption of less than 0.1 to 2 watts.

In other forms as already noted, the convection generator 26 may be a means to vibrate or otherwise regularly to move the surface with respect to the fluid being sampled and thus creating significant fluid velocity at the surface.

When one uses convection generating means 26 to vibrate surface 12 with respect to environment 16, back and forth in a direction perpendicular to surface 12, then preferred vibration values on the order of about 5000 cycles/sec (with an amplitude of close to the width or diameter of surface 12) will provide suitable air velocities at surface 12 for operating an inventive device 10. The amplitude of this back and forth vibration represents the total of the amplitude of the vibration in one direction and in the opposite direction.

Alternatively, the convection generator 26 can be a fan held in place near the surface 12, which generates air velocities in excess of 100's of feet per minute at the surface 12 supporting sampling rates of upwards of 100 ml per min per cm$^2$ of exposed area of the surface 12. Suitable small fans are commercially available, such as are used for computer disk drives.

Preferred embodiments of the invention can be mounted on a member such as thin plastic badge 36 and releasably fastened onto a user's clothing such as by fastener 38.

Collector

Again with reference to FIG. 1, the collector 18 serves as a trap for preferentially trapping chemical species for the environment and may take a variety of shapes and be formed from a variety of materials. Typically the material forming the collector 18 will absorb the chemical species of interest. Thus, for example, activated carbon, silica gel, or porous polymer adsorbents may be combined with a chemical binder to form a composite disc as collector 18. This may be, for example, on the order of about 1 to 10 mm in thickness and about 1 to 20 mm in diameter. Alternately, the adsorbent may be coated with one or more reagent chemicals designed to bind and retain the contaminants or components to be sampled. Still other illustrative alternatives are where the collector 18 is composed of paper, fiberglass, or a fabric coated with one or more reagent chemicals designed to bind and retain the components or contaminants to be sampled.

Aspects of the invention will now be illustrated with reference to the following experimental description and examples, to illustrate, but not to limit the invention.

EXPERIMENTAL

Embodiments of the invention were prepared for testing with surface areas of two or three $cm^2$ formed from inert plastic components (such as polypropylene, polyester, and the like) which were snap fit together to enclose microporous plastic membranes adjacent to the sample collector. The distance from the surface interface to the collector was 0.03 to 0.10 mm. The collector was coconut charcoal held together with an organic binder.

Embodiments of the invention were placed in an exposure chamber into which air containing known concentrations of common air contaminants were passed. To serve as a reference, the concentrations of contaminants were analyzed by continuously drawing a sample of the air to which samplers were being exposed into traditional carbon tube samplers using calibrated, external pump air samplers.

The results of these experiments are shown in Table 2. It is seen from this data that diffusional sampling rates on the order of 100 milliliter per minute per square centimeter of sampler surface were achieved.

TABLE 2

| Chemical Analyte | Inventive Embodiment (ml/min per $cm^2$) | Degree of Increase over Table 1 Prior Art (% Increase) |
|---|---|---|
| Ethyl Ether | 65 | 1528% |
| Acetone | 57 | 1138% |
| Methylene Chloride | 40 | 872% |
| Hexane | 88 | 2352% |
| Methyl Ethyl Ketone | 75 | 1707% |
| Ethyl Acetate | 79 | 1904% |
| Tetrahydrofuran | 65 | 1506% |
| Methyl Chloroform | 68 | 1720% |
| Heptane | 104 | 3033% |
| Benzene | 92 | 1972% |
| Trichloroethylene | 88 | 2061% |
| n-Propyl Acetate | 91 | 2484% |
| Methyl Methacrylate | 103 | 2785% |
| Methyl iso-Butyl Ketone | 84 | 2422% |
| Toluene | 106 | 2334% |
| Butyl Acetate | 97 | 2425% |
| Perchloroethylene | 99 | 2945% |
| Xylene | 123 | 3403% |
| Styrene | 133 | 3409% |
| Cyclohexanone | 116 | 2858% |

As shown by the data of Table 2, an inventive embodiment provided a sampling rate per unit surface area that was greatly enhanced with respect to the three commercially available personal monitors whose sampling rates for the same twenty chemical species were given in Table 1. For example, the inventive embodiment had a sampling rate increased by about 12 to about 15 times with respect to the commercially available personal monitors tested in monitoring ethyl ether and was increased by about 23 to about 28 times in monitoring methyl methacrylate.

The twenty chemical species already used in Tables 1 and 2 were again used in collecting the data of Table 3. Calculations of actual concentrations from the milligrams found for each of these twenty as analytes were made by following the following procedures.

Standard Preparations

An authentic reference substance for each analyte was weighed into a measured volume of chromatography-grade desorption solvent (typically gas chromatography grade carbon disulfide which may have 1 to 5% of a polar adjuvant such as butyl alcohol, benzyl alcohol, or 4-chlorobenzyl alcohol) to make a stock standard solution equivalent to 1.0 mg of analyte per ml of desorption solvent. The stock standard solution was diluted to make 3 to 5 working standards in the range of 0.01 to 10 mg/ml of desorption solvent.

Sample Preparations

Each monitor being tested had the sampling wafer, or collector, removed. The sampling wafers were broken into two pieces, placed into a clean 7 ml glass vial, and capped with an inert closure. The inert closure was removed, 1.0 ml of desorption solvent was added, then the vial reclosed. One agitates the vial continuously for one hour using an orbital shaker or equivalent. Gas chromatographic analysis was then used.

Capillary Gas Chromatography ("GC") Analysis

Aliquots are injected using the following conditions:

| | |
|---|---|
| GC Columns (dual) | RT-1 (Column A) |
| | RT-Volatiles (Column B) |
| Column Size | 0.25 or 0.32 mm |
| | capillary × 50 meter |
| Injection Mode | Split (typical 20:1) |
| Injector/Detector Temp | 225° C. |
| Column Temp | Hold 3 min. 35° C. per min |
| | to 220° C.; Hold 3 min |
| Injection Volume | 1.0 ml (nominal) |

Concomitantly, measured aliquots of a blank preparation and three standard preparations were injected in the range of interest (i.e. which bracket the concentrations of the Sample Preparations).

Calculations

The analytical data was entered into an MS-DOS compatible computer system in which chromatography data handling software (ChromPerfect, Palo Alto, Calif.) had been installed. Using the software, the peak areas obtained were compared from each sample preparation to the best-fit calibration curve obtained from at least four each standard preparation, and analyte concentrations in the sample preparations were computed.

We calculated exposure levels from analyte concentration as follows:

$$\text{EXPOSURE LEVEL (ppm)} = \frac{1000\,(C)\,(S)\,(R)}{(DE)\,(M)\,(SR)\,(T)}$$

where

C=Analyte Concentration (mcg/ml)
S=Volume of Solvent (ml)
R=Molar Volume at 22° C.(24.11/mole)
DE=De-sorption Efficiency (fraction of extraction)
M=Analyte Molecular Wt (g/mole)
SR=Monitor Sampling Rate (ml/min)
T=Sampling Time (min)

The actual permissible exposure limits in parts per million of the 20 compounds for which data has already been given in Tables 1 and 2 are set out in Table 3. As seen by Table 3, the sampling rate ("SR") for an embodiment of the invention as has already been described were on the order of greater than about 111 cc/min and up to almost 400 cc/min for styrene. These sampling rates compare favorably with systems using pumps, but provide the advantages of small size and weight. Table 3 also shows the calculated amount of milligrams for each of the 20 compounds at the "PEL" and shows the actual amount of mg/mil found in $CS_2$ solvent during the analysis.

TABLE 3

| CHEMICAL ANALYTE | PEL (ppm) | SR (cc/min) | mg @ PEL | mg/ml $CS_2$ |
|---|---|---|---|---|
| Ethyl Ether | 400 | 172 | 100 | 50.0 |
| Acetone | 750 | 160 | 136 | 68.2 |
| Methylene Chloride | 500 | 111 | 92.6 | 46.3 |
| Hexane | 50 | 245 | 20.7 | 10.4 |
| Methyl Ethyl Ketone | 200 | 211 | 50.0 | 29.9 |
| Ethyl Acetate | 400 | 220 | 152 | 76.2 |
| Tetrahydrofuran | 200 | 181 | 51.2 | 25.6 |
| Methyl Chloroform | 350 | 191 | 175 | 87.5 |
| Heptane | 400 | 291 | 229 | 115 |
| Benzene | 1 | 258 | 0.396 | 0.198 |
| Trichloroethylene | 50 | 247 | 31.9 | 15.9 |
| n-Propyl Acetate | 200 | 256 | 103 | 51.3 |
| Methyl Methacrylate | 100 | 287 | 56.4 | 28.2 |
| Methyl iso-Butyl Ketone | 50 | 236 | 23.2 | 11.6 |
| Toluene | 100 | 298 | 54.0 | 27.0 |
| Butyl Acetate | 150 | 272 | 93.1 | 46.5 |
| Perchloroethylene | 25 | 276 | 22.5 | 11.2 |
| Xylene | 100 | 343 | 71.4 | 35.7 |
| Styrene | 50 | 371 | 37.9 | 19.0 |
| Cyclohexanone | 25 | 326 | 15.7 | 7.85 |

Another chemical species of interest for monitoring is formaldehyde. For such a chemical species, analysis by HPLC (rather than the above described GC analysis) would typically be used, with an illustrative determination being as follows.

Exposure Chamber, Re-circulating, for Reactive Analytes

A suitable exposure chamber for reactive analytes can be formed from a chemically-inert glass, polypropylene, or fluorocarbon-coated vessel fitted with the following components.

(1) Sample introduction port allowing entry of test fixture.

(2) Analyte generator within chamber or attached to entry port.

(3) Inert air tunnel within chamber with ventilation fan allowing contents of chamber to be re-circulated through the air tunnel and across test samples.

(4) Removable test fixture to hold monitors vertically in air tunnel.

(5) Reference sampling tube (such as inert polypropylene tubing), connecting an external reference sampling port to the inside of the air tunnel in the immediate vicinity of the test fixture such that a continuous air sample may be removed and analyzed by an external reference method.

(6) External means for controlling and monitoring temperature of the chamber.

Continuous Analyte Generator

For aldehydes, an analyte generator can comprise an inert vessel containing, in its bottom, an aqueous/PEG solution of the analyte with an air space positioned above the solution which acts as a diffuser. Delivery of analyte is controlled by the strength of the aldehyde solution and by the rate of air passage.

Exposure Challenge

Making certain the exposure chamber is clean, actuate continuous analyte generator, ventilation fan, and temperature control, then allow the chamber to come to equilibrium. Connect reference sampling tube to external sample port fitted with calibrated air pump and impinger and sample for the entire exposure time. Analyze reference sample by reference method and calculate analyte level in ppm. Adjust the continuous analyte generator and repeat test until exposure chamber provides reference analyte level within the desired range of 0.3 to 3.0 ppm-8 hr TWA.

Select monitors representative of a manufactured lot. Remove from package and assemble as directed in the instructions for use. Arrange monitors in the test fixture so that the diffusion window is at mid-height of the air tunnel. Quickly place the test fixture in the exposure chamber such that the reference sampling tube will sample the environment in the immediate vicinity of the monitors being exposed, close to the entry port, and begin the exposure.

Reference Analyte Level

During the entire time the exposure challenge is being conducted, continue sampling the environment in the vicinity of the text fixture through the reference sampling tube via air pump and impinger as directed in the reference method. Collect and analyze impingers as directed in reference method and calculate the reference analyte level.

Evaluation of Monitors

When exposure challenge is complete, remove monitors and analyze monitors. Calculate the mean, standard deviation, and co-efficient or variation of monitor responses for each exposure challenge. Plot the mean monitor response for all monitors versus the reference analyte level for that exposure as determined by the external reference method. Determine the slope of linear regression to verify the sampling rate of the monitor. Report co-efficient of variation at the permissible exposure limit for the analyte tested and calculate results.

Reference Method

Equipment: Air sampling pump with drying tube, calibrate before and after sampling. Sampling rate at 100±200 ml/min into Micro-impingers Reagents:

(1) Absorbing solution: 1% sodium bisulfite in formaldehyde-free water (2) Formaldehyde Stock Standard: 4.0 mg/ml Formaldehyde Standard purchased from HACH (3) Formaldehyde Working Standard: (4.0 μg/ml) Approximately 800 ml formaldehyde free $D/H_2O$ is added to a 1 liter volumetric flask. Then 1.0±0.01 gm sodium bisulfite is transferred to the volumetric flask and 1 ml formaldehyde stock standard is pipetted into the flask. Mix to dissolve the bisulfite qs to mark with formaldehyde free $D/H_2O$. Mix thoroughly. Working standard solution can be stored at 4° C. in a tightly capped bottle for four weeks.

(4) Chronotropic Acid Solution 1% CA in $D/H_2O$. Transfer to a brown glass bottle. Prepare fresh. Do not store longer than 1 week. Blank increases with storage.

(5) Conc. Sulfuric Acid

Calibration Curve:

| Formaldehyde Bisulfite (μg) | Working Std. (ml) | (ml) |
| --- | --- | --- |
| 0.0 | 1.5 | 0.0 |
| 0.8 | 1.3 | 0.2 |
| 1.6 | 1.1 | 0.4 |
| 2.4 | 0.9 | 0.6 |
| 3.2 | 0.7 | 0.8 |
| 4.0 | 0.5 | 1.0 |
| 6.0 | 0.0 | 1.5 |

Assay Procedure:

(1) Accurately pipet 1.5 ml of the Absorbing solution from each impinger to labelled test tubes. In high levels of. formaldehyde exposure, absorbing solution should be diluted with 1% bisulfite.

(2) Pipet 0.5 ml 1% CA into each tube, vortex to mix.

(3) Add 3.0 ml conc. $H_2SO_4$, vortex to mix.

*Caution: Extremely hot! Wear protective glasses and gloves.

(4) Allow to cool to room temperature. Measure Absorbance at 580 nm in 12 cm cuvette.

It is to be understood that while the invention has been described above in conjunction with preferred specific embodiments, the description and examples are intended to illustrate and not limit the scope of the invention, which is defined by the scope of the appended claims.

It is claimed:

1. An environmental fluid sampling device, comprising:

a chamber defining a fluid diffusion pathway wherein fluid introduced from a fluid environment into the pathway adjacent to a pathway first end diffuses along the pathway to a pathway second end;

a fluid permeable surface carried by the chamber at the pathway first end and being exposed to the fluid environment;

a sample collector in fluid communication with the pathway at the pathway second end and adapted to collect chemical species carried by the fluid at a sampling rate from which concentration of the species in the fluid environment is determinable; and, a motor mounted in association with the chamber and operative to effect relative movement between the surface and environmental fluid adjacent to the surface, wherein the motor rotates the surface in the fluid environment.

2. The device as in claim 1 wherein the motor rotates the surface between about 1,000 to about 15,000 r.p.m.

3. An environmental fluid sampling device, comprising:

a chamber defining a fluid diffusion pathway wherein fluid introduced from a fluid environment into the pathway adjacent to a pathway first end diffuses along the pathway to a pathway second end;

a fluid permeable surface carried by the chamber at the pathway first end and being exposed to the fluid environment;

a sample collector in fluid communication with the pathway at the pathway second end and adapted to collect chemical species carried by the fluid at a sampling rate from which concentration of the species in the fluid environment is determinable, wherein the sampling rate is at least about 10 milliliter per minute per square centimeter of surface; and, a motor mounted in association with the chamber and operative to effect relative movement between the surface and environmental fluid adjacent to the surface.

4. The device as in claim 3 or 1 wherein the surface has a thickness of to about 3 mm.

5. The device as in claim 3 wherein the fluid is air.

6. The device as in claim 3 or 1 wherein the motor rotates the surface in the fluid environment to create air velocities in excess of about 50 ft/min at the interface between the surface and the fluid environment.

7. The device as in claim 3 or 1 wherein the fluid permeable surface is formed by a polymer with tortuous interstices.

8. The device as in claim 3 or 1 wherein the collector is absorbent or adsorbent for the chemical species.

9. An assembly, useful as a personal monitor for sampling species in environmental air, comprising:

a chamber in which species passing therein through a permeable surface is collected by gaseous diffusion;

a direct current motor; and, a motor mount adapted to operatively associate the chamber with the motor so as to move the surface when the motor is operated.

10. The assembly as in claim 9 wherein the motor is operated to rotate the surface.

11. The assembly as in claim 10 wherein the motor is operated with a battery.

12. The assembly as in claim 11 wherein the battery is from about 0.5 to about 10 volts.

13. The assembly as in claim 10 wherein the surface defines a thickness of between about 0.01 mm to about 3 mm.

14. The assembly as in claim 13 wherein the surface has an area of between about 0.1 $cm^2$ to about 10 $cm^2$.

15. The assembly as in claim 10 wherein the motor rotates the surface in the range of between about 1,000 rpm to about 15,000 rpm.

16. The assembly as in claim 9 wherein the permeable surface is formed by a polymer with tortuous porosity.

17. The assembly as in claim 16 wherein the permeable surface is formed by a β-irradiated, chemically etched membrane.

* * * * *